United States Patent
McCarthy

(10) Patent No.: US 8,026,425 B2
(45) Date of Patent: Sep. 27, 2011

(54) SWEET PEPPER HYBRID 9942595

(75) Inventor: William McCarthy, Ft. Myers, FL (US)

(73) Assignee: Seminis Vegetable Seeds, Inc., Woodland, CA (US)

( * ) Notice: Subject to any disclaimer, the term of this patent is extended or adjusted under 35 U.S.C. 154(b) by 415 days.

(21) Appl. No.: 12/419,143

(22) Filed: Apr. 6, 2009

(65) Prior Publication Data

US 2009/0255012 A1    Oct. 8, 2009

Related U.S. Application Data

(60) Provisional application No. 61/042,664, filed on Apr. 4, 2008.

(51) Int. Cl.
*A01H 5/00* (2006.01)
*A01H 5/10* (2006.01)
*A01H 5/08* (2006.01)
*C12N 5/04* (2006.01)
*C12N 15/10* (2006.01)

(52) U.S. Cl. ............ 800/317.1; 800/265; 800/278; 435/6.1; 435/410; 435/430.1

(58) Field of Classification Search .......... None
See application file for complete search history.

(56) References Cited

U.S. PATENT DOCUMENTS 5,262,316 A   11/1993   Engler et al. .......... 435/172.3
7,087,819 B2   8/2006   Edwards .............. 800/317.1

OTHER PUBLICATIONS

PI 632919 (Charleston Belle) deposited 2002.*
PI 617085 (Emerald Giant) deposited 1963.*
PI 639641 (Papryka) deposited 2000.*
U.S. Appl. No. 12/183,746, filed Jul. 31, 2008, Leij.
U.S. Appl. No. 12/183,753, filed Jul. 31, 2008, Leij.
U.S. Appl. No. 12/183,759, filed Jul. 31, 2008, Leij.
U.S. Appl. No. 12/370,502, filed Feb. 12, 2009, McCarthy.
U.S. Appl. No. 12/419,124, filed Apr. 6, 2009, McCarthy.
Berke, "Hybrid seed production in capsicum," *J. of New Seeds*, 1(3/4):49-67, 1999.
Jones et al., "A non-hypersensitive resistance in pepper to the bacterial spot pathogen is associated with two recessive genes," *Phytopathology*, 92(3):273-277, 2002.
Lane et al., "'Dempsey', a virus and bacterial spot resistant bell pepper," *Hortscience*, 32(2):333-334, 1997.
Panda et al., "Cytomorphology of induced octoploid chili pepper (*Capsicum annuum*L.)," *Theor. Appl. Gene.*, 68(6):567-577, 1984.
Pickersgill, "Genetic resources and breeding of *Capsicum* ssp.," *Euphytica*, 96:129-133, 1997.
U.S. Application for Plant Variety Protection for Pepper Variety (*Capsicum annuum* SBR991260, dated May 27, 2008.

* cited by examiner

*Primary Examiner* — David T Fox
(74) *Attorney, Agent, or Firm* — SNR Denton US LLP; Alissa Eagle, Esq.

(57) ABSTRACT

The invention provides seed and plants of the pepper hybrid 9942595 and the parent lines thereof. The invention thus relates to the plants, seeds and tissue cultures of pepper hybrid 9942595 and the parent lines thereof, and to methods for producing a pepper plant produced by crossing such plants with themselves or with another pepper plant, such as a plant of another genotype. The invention further relates to seeds and plants produced by such crossing. The invention further relates to parts such plants, including the fruit and gametes of such plants.

35 Claims, No Drawings

US 8,026,425 B2

SWEET PEPPER HYBRID 9942595

CROSS-REFERENCE TO RELATED APPLICATIONS

This application claims the priority of U.S. Provisional Application Ser. No. 61/042,664, filed Apr. 4, 2008, the entire disclosure of which is incorporated herein by reference.

FIELD OF THE INVENTION

The present invention relates to the field of plant breeding and, more specifically, to the development of sweet pepper hybrid 9942595 and of the inbred pepper lines SBR 99-1260 and SBY 99-1201.

BACKGROUND OF THE INVENTION

The goal of vegetable breeding is to combine various desirable traits in a single variety/hybrid. Such desirable traits may include greater yield, resistance to insects or pests, tolerance to heat and drought, better agronomic quality, higher nutritional value, growth rate and fruit properties.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different genotypes produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new lines and hybrids produced therefrom are evaluated to determine which of those have commercial potential.

One crop which has been subject to such breeding programs and is of particular value is the sweet pepper. As used herein, sweet pepper refers to the fruit and the plant of the non-pungent chile pepper varieties. Sweet peppers belong to the genre *Capsicum*, of the nightshade family, Solanaceae. The term "sweet pepper" therefore includes bell peppers (*Capsicum annuum*), the "Thai sweet"—also a cultivar of *C. annuum*, the "dulce"—a popular cultivar of *Capsicum baccatum*, as well as Numex Suave Orange (*Capsicum chinense*), an unusually sweet habanero-type pepper.

Sweet peppers are primarily used as vegetables in cuisine around the world; however, they are also grown for ornamental and medicinal uses. The sweet pepper fruit is eaten cooked or raw. In contrast to the hot pepper, the sweet pepper contains little, if any, capsaicin (8-methyl-N-vanillyl-6-nonenamide), the main active ingredient responsible for the pungency of hot peppers.

*C. annuum* is a herbaceous annual. The plant has a densely branched stem and grows to 1.5 to 5 feet in height. The fruit is green when unripe, then usually changing to red or brown. The species can grow in many climates; however, they thrive in warm and dry climates.

Most sweet pepper breeding programs have concentrated on the non-pungent varieties of *C. annuum*, especially bell peppers. Pickersgill and Barbara (1997). Breeding pepper lines with differently colored fruit has been very popular. The color of the fruit can be green, red, yellow, orange and, more rarely, white, purple and brown depending both on the cultivar and the time of harvest.

Peppers with multiple resistances to several pests and diseases have also been bred. Id. Pickersgill and Barbara (1997). In the case of bell peppers, the development of molecular markers and a molecular linkage map for *C. annuum* has eased some of the problems associated with selecting simultaneously for multiple resistances and other desirable characteristics. Id. Pickersgill and Barbara (1997). Other sweet pepper breeding efforts have often focused on creating non-pungent cultivars of hot peppers. See e.g. U.S. Pat. No. 7,087,819.

Tetraploidy and haploidy are relatively easy to induce in *Capsicum* species. In fact, an octaploid *Capsicum annuum* was recently reported (Panda et al., 1984). *Capsicum* species exhibit barriers to interspecific gene transfer. These include unilateral incompatibility, post-fertilization abortion, and nucleo-cytoplasmic interactions leading to male sterility or other abnormalities (Pickersgill and Barbara, 1997). However, the development of a pepper line resistant to the anthracnose fungal pathogen using interspecific crossing between *Capsicum baccatum* and *C. annuum* has been reported (Chae et al., 2003).

Hybrid vigor has also been documented in peppers, and hybrids are gaining increasing popularity among farmers throughout the world, especially in countries with plentiful labor (Berke, 1999).

While breeding efforts to date have provided a number of useful sweet pepper lines with beneficial traits, there remains a great need in the art for new lines with further improved traits. Such plants would benefit farmers and consumers alike by improving crop yields and/or quality.

SUMMARY OF THE INVENTION

The present invention overcomes limitations in the prior art by providing, for example, seeds and plants of a sweet pepper hybrid having a combination of genes, the expression of which provides a number of advantageous traits, such as anthocyaninless, green to red bell pepper fruit with an large size at maturity of about 10 cm in width and 10 cm in length, and about 200 g to about 300 g. Other advantageous traits include resistance to Races 1 to 3 Bacterial leaf spot (BLS), *Xanthomonas campestris* pv. *vesicatoria*, and Tobacco etch virus (TEV). Sweet pepper hybrid 9942595 has some tolerance to *Phytophthora capsici*. This represents a significant advance in the art by offering resistance to BLS, TEV, and tolerance to *Phytophthora capsici* combined with the anthocyaninless trait, and excellent fruit qualities.

In one aspect, the present invention provides a pepper plant of the hybrid designated 9942595 and/or pepper lines SBR 99-1260 and SBY 99-1201. Also provided are pepper plants having all the physiological and morphological characteristics of the pepper hybrid 9942595. Parts of the sweet pepper plant of the present invention are also provided, for example, including pollen, an ovule, scion, a rootstock, a fruit, and a cell of the plant.

In another aspect, the invention provides a plant of a sweet pepper hybrid that exhibits a combination of traits comprising resistance Races 1 to 3 Bacterial leaf spot (BLS), *Xanthomonas campestris* pv. *vesicatorial*, and Tobacco etch virus (TEV), and anthocyaninless. In certain embodiments, the combination of traits may be defined as controlled by genetic means for the expression of the combination of traits found in sweet pepper hybrid 9942595.

The invention also concerns the seed of pepper hybrid 9942595 and/or pepper lines SBR 99-1260 and SBY 99-1201. The pepper seeds of the invention may be provided as an essentially homogeneous population of pepper seed of pepper hybrid 9942595 and/or pepper lines SBR 99-1260 and SBY 99-1201. Essentially homogeneous populations of seed are generally free from substantial numbers of other seed. Therefore, seed may be defined as forming at least about 97% of the total seed, including at least about 98%, 99% or more of the seed. The seed population may be separately grown to provide an essentially homogeneous population of pepper plants designated pepper hybrid 9942595 and/or pepper lines SBR 99-1260 and SBY 99-1201.

In another aspect of the invention, a plant of pepper hybrid 9942595 and/or pepper lines SBR 99-1260 and SBY 99-1201 comprising an added heritable trait is provided. The heritable trait may comprise a genetic locus that is, for example, a dominant or recessive allele. In one embodiment of the invention, a plant of pepper hybrid 9942595 and/or pepper lines SBR 99-1260 and SBY 99-1201 is defined as comprising a single locus conversion. In specific embodiments of the invention, an added genetic locus confers one or more traits such as, for example, herbicide tolerance, insect resistance, disease resistance, and modified carbohydrate metabolism. In further embodiments, the trait may be conferred by a naturally occurring gene introduced into the genome of the line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

In another aspect of the invention, a tissue culture of regenerable cells of a pepper plant described herein is provided. The tissue culture will preferably be capable of regenerating pepper plants capable of expressing all of the physiological and morphological characteristics of the line, and of regenerating plants having substantially the same genotype as other plants of the line. Examples of some of the physiological and morphological characteristics include those traits set forth in the tables herein. The regenerable cells in such tissue cultures may be derived, for example, from embryos, meristems, cotyledons, pollen, leaves, anthers, roots, root tips, pistil, flower, seed and stalks. Still further, the present invention provides pepper plants regenerated from a tissue culture of the invention, the plants having all the physiological and morphological characteristics of a plant provided herein.

In yet another aspect of the invention, processes are provided for producing pepper seeds, plants and fruit, which processes generally comprise crossing a first parent pepper plant with a second parent pepper plant, wherein at least one of the first or second parent pepper plants is a plant of pepper line SBR 99-1260 and pepper line SBY 99-1201. These processes may be further exemplified as processes for preparing hybrid pepper seed or plants, wherein a first pepper plant is crossed with a second pepper plant of a different, distinct genotype to provide a hybrid that has, as one of its parents, a plant of the pepper line SBR 99-1260 or pepper line SBY 99-1201. In these processes, crossing will result in the production of seed. The seed production occurs regardless of whether the seed is collected or not.

In one embodiment of the invention, the first step in "crossing" comprises planting seeds of a first and second parent pepper plant, often in proximity so that pollination will occur for example, mediated by insect vectors. Alternatively, pollen can be transferred manually. Where the plant is self-pollinated, pollination may occur without the need for direct human intervention other than plant cultivation.

A second step may comprise cultivating or growing the seeds of first and second parent pepper plants into plants that bear flowers. A third step may comprise preventing self-pollination of the plants, such as by emasculating the flowers, (i.e., killing or removing the pollen). Self-incompatibility systems may also be used in some hybrid crops for the same purpose. Self-incompatible plants still shed viable pollen and can pollinate plants of other varieties but are incapable of pollinating themselves or other plants of the same genotype.

A fourth step for a hybrid cross may comprise cross-pollination between the first and second parent pepper plants. Yet another step comprises harvesting the seeds from at least one of the parent pepper plants. The harvested seed can then be grown to produce a pepper plant.

The present invention also provides the pepper seeds and plants produced by a process that comprises crossing a first parent pepper plant with a second parent pepper plant, wherein at least one of the first or second parent pepper plants is a plant of pepper hybrid 9942595 and/or pepper lines SBR 99-1260 and SBY 99-1201. In one embodiment of the invention, pepper seed and plants produced by the process are first generation ($F_1$) hybrid pepper seed and plants produced by crossing a plant in accordance with the invention with another, distinct plant. The present invention further contemplates plant parts of such an $F_1$ hybrid pepper plant, and methods of use thereof. Therefore, certain exemplary embodiments of the invention provide an F1 hybrid pepper plant and seed thereof.

In still yet another aspect, the present invention provides a method of producing a plant derived from hybrid 9942595 and/or pepper lines SBR 99-1260 and SBY 99-1201, the method comprising the steps of: (a) preparing a progeny plant derived from hybrid 9942595 and/or pepper lines SBR 99-1260 and SBY 99-1201, wherein said preparing comprises crossing a plant of the hybrid 9942595, pepper line SBR 99-1260 or pepper line SBY 99-1201 with a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from hybrid 9942595, pepper line SBR 99-1260 or pepper line SBY 99-1201. The plant derived from hybrid 9942595, pepper line SBR 99-1260 or pepper line SBY 99-1201 may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from hybrid 9942595 and/or pepper lines SBY 99-1201 and SBR 99-1260 is obtained which possesses some of the desirable traits of the starting plant as well as potentially other selected traits.

In certain embodiments, the present invention provides a method of producing peppers comprising: (a) obtaining a plant of pepper hybrid 9942595 and/or pepper lines SBR 99-1260 and SBY 99-1201, wherein the plant has been cultivated to maturity, and (b) collecting peppers from the plant.

In still yet another aspect of the invention, the genetic complement of pepper hybrid 9942595 and/or pepper lines SBR 99-1260 and SBY 99-1201 is provided. The phrase "genetic complement" is used to refer to the aggregate of nucleotide sequences, the expression of which sequences defines the phenotype of, in the present case, a pepper plant, or a cell or tissue of that plant. A genetic complement thus represents the genetic makeup of a cell, tissue or plant, and a hybrid genetic complement represents the genetic make up of a hybrid cell, tissue or plant. The invention thus provides pepper plant cells that have a genetic complement in accordance with the pepper plant cells disclosed herein, and plants and seeds containing such cells.

Plant genetic complements may be assessed by genetic marker profiles, and by the expression of phenotypic traits that are characteristic of the expression of the genetic complement, e.g., isozyme typing profiles. It is understood that pepper hybrid 9942595 and/or pepper lines SBR 99-1260 and SBY 99-1201 could be identified by any of the many well known techniques such as, for example, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

In still yet another aspect, the present invention provides hybrid genetic complements, as represented by pepper plant cells, tissues, plants, and seeds, formed by the combination of a haploid genetic complement of a pepper plant of the invention with a haploid genetic complement of a second pepper plant, preferably, another, distinct pepper plant. In another aspect, the present invention provides a pepper plant regenerated from a tissue culture that comprises a hybrid genetic complement of this invention.

In still yet another aspect, the invention provides a method of determining the genotype of a plant of pepper hybrid 9942595 and/or pepper lines SBR 99-1260 and SBY 99-1201 comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The invention further provides a computer readable medium produced by such a method.

Any embodiment discussed herein with respect to one aspect of the invention applies to other aspects of the invention as well, unless specifically noted.

The term "about" is used to indicate that a value includes the standard deviation of the mean for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

Other objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

The invention provides methods and compositions relating to plants, seeds and derivatives of sweet pepper hybrid 9942595. This hybrid can be described as producing a green to red bell pepper. Sweet pepper hybrid 9942595 exhibits a number of improved traits including a small to medium plant size, golden yellow anthers and anthocyaninless. Anthocyanin is not observed in either the fruit or the stem. The mature fruit of the line can be further characterized as being firm and having a weight from about 200 to about 300 grams, a size that is large, and typically a blocky bell pepper shape. Average fruit dimensions at maturity are 10 cm wide by 10 cm long. Fruit at the green stage is dark green, while fruit at red stage is bright red. The invention also provides parent lines SBR 99-1260 and SBY 99-1201

Sweet pepper hybrid 9942595 develops a large sized plant producing firm fruit at the mature green and red stages. Fruit are smooth in appearance, and medium to dark green in color at the green stage. The main use of this hybrid would be in areas that affected by Races 1 to 3 Bacterial leaf spot (BLS), *Xanthomonas campestris* pv. *vesicatorial*, and/or affected by severe Tobacco etch virus (TEV). Sweet pepper hybrid 9942595 has some tolerance to *Phytophthora capsici*. This combination of traits makes sweet pepper hybrid 9942595 desirable for growers as it allows them to continue to grow and harvest peppers in areas affected by one or more of the diseases BLS, severe TEV and *Phytophthora capsici*. Sweet pepper hybrid 9942595 also appears resistant to the Pepper mottle virus. The hybrid is primarily intended for open field production. This hybrid shows uniformity and stability within the limits of environmental influence for the traits described hereinafter. Sweet pepper hybrid 9942595 provides sufficient seed yield.

This hybrid is suitable for production is several areas, but was primarily developed for cultivation in western Mexico. It may also be adapted for Venezuela, S. Africa, Thailand, Australia, parts of the Caribbean, other parts of Mexico and the United States of America (USA). The development of the hybrid and its parent lines can be summarized as follows.

A. Origin and Breeding History of Sweet Pepper Hybrid 9942595

The parents of sweet pepper hybrid 9942595 are pepper line SBR 99-1260 and pepper line SBY 99-1201. These parents were both created at breeding stations in Felda, Fla. TEV resistance was provided by line SBR 99-1200. *Phytophthora capsici* resistance was originally provided by line SBR 99-1200.

SBR 99-1260 was developed by pedigree selection from a cross between parent lines SBR 99-1200 and 7274384-M-2-1-1-1-2.00LB 8884-02. SBR 99-1200 is a blocky bell fixed for severe Tobacco etch virus (TEV) resistance via the pvr 1 gene, and fixed for resistance to races 1-3 of Bacterial leaf spot (*Xanthomonas campestris* pv. *vesicatoria*) via the Bs2 gene, with intermediate resistance to *Phytophthora capsici*. SBR 99-1260 is characterized by a large plant, with dark green fruit color, and large to extra-large fruit size. Parent 7274384-M-2-1-1-1-2.00LB 8884-02 is a blocky bell fixed for TMV(Po) resistance, Potato virus Y pathotype P0 (PVY) resistance via the pvr2-2 gene, and is anthocyaninless. Neither parent was marketed directly as open pollinated lines. SBR 99-1260 differs from SBR 99-1200 because it has TMV (P0) resistance, and is anthocyaninless, and differs from 7274384-M-2-1-1-1-2.00LB 8884-02 because it has intermediate resistance to *Phytophthora capsici*, and is fixed for TEV resistance. The crossing and selections that led to the development of SBR 99-1260 were as follows Year 1 Planted parents SBR 99-1200 and 7274384-M-2-1-1-1-2.00LB 8884-02 in greenhouses in Florida. To produce F1 hybrid designated 9915003

Year 1 Sowed F1 Hybrid 9915003 in Florida greenhouse; plants were transplanted to a Florida field and allowed to self. Planted as stake No. 01LB 08978.

Year 2 Sowed and transplanted F2 population as stake #02LB 01165. Selected individual plants.

Year 2 Planted F3 inbred line 02LB 01165-06 as stake #02LB 07278. Tested for severe Tobacco etch virus (TEV) resistance and *Phytophthora capsici* resistance and found it to be segregating for both, but fixed for anthocyaninless. Tested line for Race 1-3 bacterial leaf (*Xanthomonas campestris* pv. *vesicatoria*) resistance and found it to be fixed susceptible. Selected individual plants.

Year 3 Planted F4 inbred line 02LB 07278-02 as stake #03LB 03867. Tested line for TMV(Po) resistance (L1 gene) and found to be fixed resistant. Tested line for *Phytophthora capsici* resistance and found to be segregating. Tested line for severe Tobacco etch virus (TEV) resistance and found to be fixed resistant. Selected individual plants.

Year 3 Planted F5 inbred line 03LB 03867-03 as stake #03LB 08520. Tested line for *Phytophthora capsici* resistance and found it to be segregating. Selected individual plants.

Year 4 Planted F6 inbred line 03LB 08520-01 as stake #04LB 02465. Tested line for *Phytophthora capsici* resistance and found it to be segregating. Selected individual plants.

Year 4 Planted F7 inbred line 04LB 02465-02 in the greenhouse as stake # LBGH 9771. Tested line for *Phytophthora capsici* resistance and found to be fixed resistant. During the growing season, the line appeared uniform and stable. Plants appeared medium sized, with large to extra-large firm fruit, with relatively early maturity, deep shoulders, and a dark red color at full maturity. The entire plot was selected and bulked.

Year 5 Planted F8 inbred line bulk 04LB LBGH 9771-M as stake #05LB 02047. Plants appeared medium sized, with a heavy set of medium-dark green fruit and very smooth blossom-end and shoulders. Fruit appeared firm at the green and red stage, with a dark red color at full maturity. The source 04LB LBGH 9771-M was submitted to foundation seed as parent SBR99-1260.

SBR 99-1260 is uniform and stable. It is within commercial acceptable limits as compared with other sweet pepper inbreds. A small percentage of variants can occur within commercially acceptable limits for almost any trait during the course of repeated multiplication. However, no variants were observed during the four times in which SBR99-1260 was observed in other trials.

SBY 99-1201 was developed in Felda Fla., by pedigree selection from Seminis hybrid PSR 370694. This hybrid resulted from a cross between 2367016092-7884 and Y225V041876-7170. Parent 2367016092-7884 is an anthocyaninless, blocky red bell fixed for Tobacco etch virus (TEV) and Tobacco mosaic virus (pathotype P0) resistance. Parent Y225V041876-7170 is a yellow, blocky bell fixed for resistance to TEV (pvr1gene), races 1, 2, and 3 bacterial spot (*Xanthomonas campestris* pv. *vesicatoria*) Bs2 gene resistance. Neither parent was marketed directly as open pollinated lines. SBY 99-1201 differs from 2367016092-7884 because it is yellow, and resistant to races 1-3 Bacterial Leaf Spot (*Xanthomonas campestris* pv. *vesicatoria*). SBY 99-1201 differs from Y225V041876-7170 because it is resistant to Tobacco mosaic virus. The crossing and selections were made as follows:

Year 1 Planted parents 2367016092-7884 and Y225V041876-7170 in a Florida greenhouse and crossed to produced a F1 Hybrid designated PSR 370694.

Year 2 Sowed F1 hybrid PSRI 370694 at Felda Station, plants were transplanted to the field in Felda and allowed to self. Planted as stake #95LB 4612.

Year 2 Planted F2 inbred line 95LB 4612 as stake #95LB 8996. A line appeared segregating for the anthocyaninless gene. Individual plants were selected.

Year 3 Planted F3 inbred line 95LB 08996-1 as stake #96LB 1795. A red-fruited line appeared fixed for the anthocyaninless trait. Individual plants were selected.

Year 3 Planted F4 inbred line 96LB 1795-10 as stake #96LB 10613. An anthocyaninless line with very large, square fruit segregating for fruit color (red/yellow) was identified with Race 1-3 bacterial spot and tobacco mosaic virus pathotype P0 resistance. Individual plants were selected.

Year 4 Planted F5 inbred line 96LB 10613-2 as stake #97LB 3318. A line fixed for yellow fruit color and segregating for resistance to the Tobacco etch virus was identified. Individual plants were selected.

Year 8 Planted F6 inbred line 97LB 3318-1 as stake #01LB 01475. Plants were appeared stable and uniform. The line was bulked.

Year 8 Planted F7 inbred line bulk 01LB 01475-M as stake #01LB 07468. Plants appeared tall and produced a heavy, gradual set of yellow, smooth, and blocky fruit. Tests indicated the line was fixed for the Tobacco etch virus (pvr1) gene. Plants appeared stable and uniform. The line was bulked.

Year 9 Planted F8 inbred line bulk 01LB 07468-M as stake #02LB 04198. Records indicate anthocyaninless plants with yellow, blocky fruit. Plants tested as resistant to the Tobacco mosaic virus pathotype P0 (L1 gene), race 1, 2 and 3 of bacterial spot (caused by *Xanthomonas campestris* pv. *vesicatoria*), and to the Tobacco etch virus (pvr1gene). The line was bulked.

SBY 99-1201 is uniform and stable. It is within commercial acceptable limits as is true with other Sweet Pepper inbreds. A small percentage of variants can occur within commercially acceptable limits for almost any character during the course of repeated multiplication. However no variants were observed, during the four times in which SBY 99-1201 was observed in other trials.

B. Physiological and Morphological Characteristics of Pepper Hybrid 9942595

In accordance with one aspect of the present invention, there is provided a plant having the physiological and morphological characteristics of sweet pepper hybrid 9942595. A description of the physiological and morphological characteristics of sweet pepper hybrid 9942595 is presented in Table 1.

TABLE 1

Physiological and Morphological Characteristics of Pepper Hybrid 9942595

| CHARACTERISTIC | HYBRID 9942595 |
|---|---|
| Species | *C. annuum* |
| Mature Plant | |
| Days from Transplanting until Green Stage | 75 |
| Days from Transplanting until Red/Yellow Stage | 90 |
| Plant Habit | Spreading |
| Plant Attitude | Upright/Erect |
| Height | Very Tall |
| Basal Branches | Few (2-3) |
| Branch Flexibility | Rigid |
| Stem Strength (Breakage Resistance) | Intermediate |
| Leaf | |
| Length of Blade | Medium |
| Width of Blade | Broad |
| Color | Dark Green |
| Intensity of Green Color | Medium |
| Mature Leaf Shape | Broad Elliptic |
| Leaf and Stem Pubescence | Light |
| Undulation of Margin | Weak |
| Profile in Cross Section | Flat |
| Glossiness | Medium |
| Peduncle Attitude | Drooping |
| Flower | |
| Corolla Color | White |
| Anther Color | Yellow |
| Self-Incompatibility | Absent |
| Fruit | |
| Group | Bell (Yolo Wonder L.) |
| Color (Before Maturity) | Green |
| Intensity of Color (Before Maturity) | Dark |
| Color (Immature Fruit) | Dark Green |
| Attitude/Position | Drooping/Pendent |
| Length | Medium |
| Diameter | Very Broad |
| Ratio Length/Diameter | Medium |
| Diameter at Mid-Point | 1000.0 mm |
| Flesh Thickness at Mid-Point | 7.0 mm |
| Average Number of Fruits per Plant | 10 |
| Average Weight | 250 gm |
| Shape in Longitudinal Section | Square |
| Shape in Cross-Section (Level of Placenta) | Quadrangular |
| Texture of Surface | Smooth/Very Slightly Wrinkled |
| Color (Mature) | Red |
| Glossiness | Medium |
| Shape of Apex | Moderately Depressed |
| Shape | Bell (Yolo Wonder L.) |
| Set | Scattered |
| Depth of Interloculary Grooves | Shallow |
| Number of Locules | Predominately four and More |
| Measurement with Three Locules | 50% |
| Measurement with Four Locules | 40% |
| Measurement with Five or More | 10% |
| Thickness of Flesh | Very Thick |

TABLE 1-continued

Physiological and Morphological Characteristics of Pepper Hybrid 9942595

| CHARACTERISTIC | HYBRID 9942595 |
|---|---|
| Calyx: Aspect | Non-Enveloping/Saucer-Shaped |
| Pungency | Sweet |
| Capsaicin in Placenta | Absent |
| Flavor - Dry Fruit | Mild Pepper |
| Glossiness - Dry Fruit | Moderate |
| Seed | |
| Color | Yellow |
| Anthocyanin Coloration of Hypocotyl | Absent |
| Plant | |
| Anthocyanin Coloration of Stem | Absent |
| Anthocyanin Coloration of Nodes | Absent |
| Stem: Intensity of Anthocyanin Coloration of Nodes | Very Weak |
| Anthocyanin Coloration of Leaf | Absent |
| Flower: Anthocyanin Coloration in Anther | Absent |
| Fruit: Anthocyanin Coloration | Absent |
| Time of Maturity | Late |
| Diseases | |
| Resistance to Tobamovirus Pathotype 0 | Most Resistant |
| Resistance to Potato virus Y | Most Resistant |
| PVY Pathotype 0 | Present - Most Resistant |
| PVY Pathotype 1 | Present - Most Resistant |
| PVY Pathotype 1-2 | Present - Most Resistant |
| Resistance to Tobacco Etch Virus | Most Resistant |
| Resistance to Cucumber Mosaic Virus (CMV) | Absent |
| Resistance to *Xanthomonas campestris* pv. *vesicatoria* | Present - Most Resistant |
| Resistance to Severe Tobacco Etch Virus | Most Resistant |

*These are typical values. Values may vary due to environment. Other values that are substantially equivalent are within the scope of the invention.

The parents of hybrid 9942595, SBR 99-1260 and SBY 99-1201, have been self-pollinated and planted for a number of generations to produce the homozygosity to make the hybrid 9942595 phenotypically stable and commercial useful. No variant traits have been observed or are expected for the parents of this hybrid.

C. Physiological and Morphological Characteristics of Breeding Sweet Pepper SBR99-1260

The hybrid 9942595 was produced by crossing inbred SBR 99-1260 with SBY 99-1201. A description of the physiological and morphological characteristics of pepper lines SBR 99-1260 and SBY 99-1201 are presented in Tables 2 and 3.

TABLE 2

Physiological and Morphological Characteristics of Pepper SBR 99-1260

| CHARACTERISTIC | SBR 99-1260 |
|---|---|
| Species | *C. annuum* |
| Mature Plant | |
| Plant Habit | compact |
| Plant Attitude | semi-upright/semi-erect |
| Measurement: Plant height | 61.0 cm |
| Measurement: Plant width | 45.7 cm |
| Measurement: length of stem from cotyledon to first flower | 15.9 cm |
| Measurement: length of the third internode (from soil surface) | 102.7 cm |
| Plant: length of stem | medium |
| Plant: shortened internode | absent |

TABLE 2-continued

Physiological and Morphological Characteristics of Pepper SBR 99-1260

| CHARACTERISTIC | SBR 99-1260 |
|---|---|
| Stem: hairiness of nodes | absent or very weak |
| Plant: height | medium |
| Plant: basal branches | few (2-3) |
| Plant: branch Flexibility | willowy |
| Plant: stem strength (breakage resistance) | intermediate |
| Leaf | |
| Length of Blade | medium |
| Width of Blade | Broad |
| Leaf width | 41.3 cm |
| Leaf length | 95.2 cm |
| Petiole length | 28.8 cm |
| Leaf color | medium green |
| Intensity of Green Color (RHS color chart value) | medium |
| Mature leaf shape | broad elliptic |
| leaf and stem pubescence | absent |
| Undulation of margin | very week |
| Leaf: blistering | medium |
| Profile in Cross Section | Moderately convex |
| Glossiness | Medium |
| Peduncle Attitude | Drooping |
| Flower | |
| Flowers per leaf axil | 1 |
| Calyx lobes | 7 |
| Petals | 7 |
| Flower diameter | 25.4 mm |
| Corolla Color | White |
| Corolla throat markings | Yellow |
| Anther Color | Yellow |
| Flower: style length | Less than stamen |
| Self-Incompatibility | Absent |
| Fruit | |
| Group | Bell (Yolo Wonder L.) |
| Color (Before Maturity) | green |
| Intensity of Color (Before Maturity) | medium |
| Color (Immature Fruit) | medium green |
| Attitude/Position | drooping/pendent |
| Length | medium |
| Diameter | broad |
| Ratio Length/Diameter | small |
| Calyx diameter | 34.9 mm |
| Fruit length | 101.6 mm |
| Fruit diameter at calyx attachment | 63.5 mm |
| Fruit diameter at mid-point | 101.6 mm |
| Flesh thickness at mid-point | 6.4 mm |
| Average number of fruits per plant | 10 |
| Fruit: % large fruits | 17%, weight range 150 to 250 |
| Fruit: % medium fruits | 56%, weight range 100 to 140 |
| Fruit: % small fruits | 27%, weight range 80 to 96 |
| Average fruit weight | 120.6 gm |
| Fruit: shape in longitudinal section | square |
| Fruit: shape in cross section (at level of placenta) | quadrangular |
| Fruit: texture of surface | Smooth or very slightly wrinkled |
| Fruit: color (at maturity) | red |
| Fruit: intensity of color (at maturity) | dark |
| Fruit: glossiness | Medium/moderate |
| Fruit: stalk cavity | absent |
| Fruit: pedicel length | 41.3 mm |
| Fruit: pedical thickness | 6.4 mm |
| Fruit: pedical shape | curved |
| Fruit: pedical cavity | absent |
| Stalk: length | medium |
| Stalk: thickness | thick |
| Fruit: base shape | cupped |
| Fruit: shape of apex | blunt |
| Fruit: shape | Bell (Yolo Wonder L.) |
| Fruit set | concentrated |
| Fruit: depth of interloculary grooves | shallow |
| Fruit: number of locules | Predominantly four and more |
| Fruit: % with one locule | 0% |
| Fruit: % with two locules | 0% |
| Fruit: % with three locules | 35% |
| Fruit: % with four locules | 65% |
| Fruit: % with five or more locules | 0% |
| Fruit: average number of locules | 3.6% |
| Fruit: thickness of flesh | thick |
| Calyx: aspect | Non-enveloping/saucer-shaped |
| Fruit: pungency | Sweet |
| Fruit: capsaicin in placenta | absent |
| Fruit: flavor | Mild pepper flavor |
| Fruit: glossiness | moderate |
| Seeds | |
| Seed cavity length | 76.2 mm |
| Seed cavity diameter | 92.1 mm |
| Placenta length | 28.6 mm |
| Number of seeds per fruit | 175 |
| Grams per 1000 seeds | 8.1 gm |
| Seed color | yellow |
| Seedling: anthocyanin coloration of Hypocotyl | absent |
| Plant: anthocyanin coloration of stem | absent |
| Plant: anthocyanin coloration of nodes | weak |
| Stem: intensity of anthocyanin coloration of nodes | very weak |
| Plant: anthocyanin coloration of leaf | absent |
| Plant: anthocyanin coloration of pedicel | absent |
| Plant: anthocyanin coloration of calyx | absent |
| Flower: anthocyanin coloration of anther | absent |
| Fruit: anthocyanin coloration | absent |
| Beginning of flowering (1st flower on 2nd flowering node | medium |
| Time of maturity | medium |

*These are typical values. Values may vary due to environment. Other values that are substantially equivalent are within the scope of the invention.

TABLE 3

Physiological and Morphological Characteristics of Pepper SBY 99-1201

| CHARACTERISTIC | SBY 99-1201 | Early Cal Wonder |
|---|---|---|
| Species | C. annuum | C. annuum |
| Maturity (in region of best adaptability) | | |
| from transplanting until mature green stage | 81 | 67 |
| from transplanting until mature red or yellow stage | 104 | 85 |
| from direct seeding until mature green stage | 118 | 104 |
| from direct seeding until mature red or yellow stage | 141 | 122 |

TABLE 3-continued

Physiological and Morphological Characteristics of Pepper SBY 99-1201

| CHARACTERISTIC | SBY 99-1201 | Early Cal Wonder |
|---|---|---|
| Plant | | |
| habit | compact | compact |
| attitude | upright/erect (De Cayenne, Doux très long des Landes, Piquant d'Algérie | upright/erect |
| height | 48.6 cm | 40.9 cm |
| width | 41.0 cm | 47.1 cm |
| length of stem from cotyledon to first flower | 17.1 cm | 10.7 cm |
| measurements length of the third internode (from soil surface) | 94.3 mm | 54.0 mm |
| length of stem | long (Lipari, Marconi, Rouge long ordinaire) | |
| plant: shortened internode (in upper part) | absent (California wonder, De Cayenne) | |
| for varieties without shortened internodes only: plant: length of internode (on primary side shoots) | long (Corno di toro rosso) | |
| stem: hairiness of nodes | absent or very weak (Arlequin) | |
| plant: height | tall (Century, Orias) | |
| plant: basal branches | few (2-3) | few |
| plant: branch flexibility | rigid (Yolo Wonder) | rigid |
| plant: stem strength (breakage resistance) | strong | intermediate |
| leaf: length of blade | long (Cupido, Dolmy, Encore, Mazurka, Monte) | |
| leaf: width of blade | medium (Albaregia, Balaton, Danubia, Marconi, Merit) | |
| Leaf: measurements | | |
| width | 66.7 mm | 60.0 mm |
| length | 128.7 mm | 113.3 mm |
| petiole length | 56.7 mm | 46.0 mm |
| color | dark green | light green |
| color RHS Color Chart value | 139B | 147A |
| intensity of green color | dark (Dolmy, Tinto) | |
| mature leaf shape | ovate (Balico, Sonar) | ovate |
| leaf and stem pubescence | absent | absent |
| undulation of margin | very weak | absent |
| blistering | very weak | weak |
| profile in cross section | moderately concave (Doux italien, Favolor) | |
| glossiness | medium (Alby, Eolo) | |
| peduncle: attitude | semi-drooping (Blondy) | |
| Flower | | |
| number | 1 | 1 |
| calyx | 6 | 6 |
| petals | 7 | 6 |
| size diameter | 25.6 mm | 25.1 mm |
| corolla color | white | white |
| corolla throat markings | yellow | yellow |
| anther color | yellow | purple |
| style length | less than stamen | same as stamen |
| self-compatibility | absent | absent |
| Fruit | | |
| group | Bell (Yolo Wonder L.) | Bell (Yolo Wonder L.) |
| color (before maturity) | green (California wonder, Lamuyo) | |
| intensity of color (before maturity) | medium | |
| immature fruit color | medium green | medium green |
| immature fruit color RHS Color Chart value | 137A | |
| attitude/position | drooping/pendent (De Cayenne, Lamuyo) | drooping/pendent |
| length | medium (Féher, Lamuyo | |
| diameter | broad (Clovis, Lamuyo) | |
| ratio length/diameter | small (Bucano, Topgirl) | |
| calyx diameter | 30.9 mm | 32.0 mm |
| fruit length | 65.6 mm | 80.0 mm |

TABLE 3-continued

Physiological and Morphological Characteristics of Pepper SBY 99-1201

| CHARACTERISTIC | SBY 99-1201 | Early Cal Wonder |
|---|---|---|
| fruit diameter at calyx attachment | 76.3 mm | 70.0 mm |
| fruit diameter at mid-point | 82.3 mm | 80.0 mm |
| flesh thickness at mid-point | 5.8 mm | 6.0 mm |
| average number of fruits per plant | 9.1 | 10.0 |
| % large fruits | weight range: 150 to 250 gm: 24.2% | weight range: 130 to 200 gm: 50.0% |
| % medium fruits | weight range: 75 to 145 gm: 46.9% | weight range: 90 to 120 gm: 30.0% |
| % small fruits | weight range: 0 to 70 gm: 28.9% | weight range: 50 to 75 gm: 20.0% |
| average fruit weight | 119.1 gm | 100.0 gm |
| shape in longitudinal section | square (Delphin, Yolo Wonder) | square |
| shape in cross section (at level of placenta) | quadrangular | quadrangular |
| sinuation of pericarp at basal part | very weak (Delphin, Kalocsai V-2, Milord) | |
| sinuation of pericarp excluding basal part | weak (Clovis, Sonar) | |
| texture of surface | smooth or very slightly wrinkled (Milord) | smooth or very slightly wrinkled |
| color (at maturity) | yellow (Golden calwonder, Heldor) | |
| intensity of color (at maturity) | medium | |
| mature fruit color | orange-yellow | red |
| mature fruit color RHS Color Chart value | 17A | 46A |
| glossiness | medium/moderate (Carré doux extra hâtif, Lamuyo, Sonar) | medium/moderate |
| stalk cavity | present (Bingor, Lamuyo) | |
| depth of stalk cavity | shallow (Delphin, Doux italien, Fehér, Latino) | |
| pedicel length | 37.3 mm | 20.0 mm |
| pedicel thickness | 9.3 mm | 6.0 mm |
| pedicel shape | curved | curved |
| pedicel cavity | present | absent |
| depth of pedicel cavity | 3.0 mm | |
| stalk: length | medium (Fehér, Sonar | |
| stalk: thickness | medium (Doux italien, Surpas) | |
| base shape | cupped | cupped |
| shape of apex | very depressed (Kerala, Monte, Osir) | very depressed |
| shape | Bell (Yolo Wonder L.) | Bell (Yolo Wonder L.) |
| set | concentrated | scattered |
| depth of interloculary grooves | medium (Clovis, Lamuyo, Marconi) | medium |
| number of locules | predominantly four and more (Palio, PAZ szentesi) | |
| % fruits with one locule | 0% | 0% |
| % fruits with two locules | 3.3% | 0% |
| % fruits with three locules | 26.7% | 40.0% |
| % fruits with four locules | 56.7% | 60.0% |
| % fruits with five or more locules | 13.3% | 0% |
| average number of locules | 3.8 | 3.6 |
| thickness of flesh | thick (Andevalo, Bingor, Daniel, Topgirl) | |
| calyx: aspect | non-enveloping/saucer-shaped (Lamuyo, Sonar) | non-enveloping/saucer-shaped |
| pungency | sweet | sweet |
| capsaicin in placenta | absent (Sonar) | |
| flavor | mild pepper flavor | moderate |
| glossiness | moderate | shiny |
| Seed | | |
| seed cavity length | 54.2 mm | 43.0 mm |
| seed cavity diameter | 70.6 mm | 52.0 mm |
| placenta length | 25.1 mm | 22.0 mm |
| number of seeds per fruit | 185 | 100 |
| grams per 1000 seeds | 8.3 gm | 7.5 gm |
| seed color | yellow | yellow |

TABLE 3-continued

Physiological and Morphological Characteristics of Pepper SBY 99-1201

| CHARACTERISTIC | SBY 99-1201 | Early Cal Wonder |
|---|---|---|
| Seedling | | |
| anthocyanin coloration of hypocotyl | weak | moderate |
| anthocyanin coloration of stem | absent | absent |
| anthocyanin coloration of nodes | weak | weak |
| stem: intensity of anthocyanin coloration of nodes | weak (California wonder, Clio, Doux d'Espagne, Dous très long des Landes, Golden calwonder) | |
| plant: anthocyanin coloration of leaf | absent | absent |
| plant: anthocyanin coloration of pedicel | absent | absent |
| plant: anthocyanin coloration of calyx | absent | absent |
| flower: anthocyanin coloration in anther | absent (Danza) | |
| fruit: anthocyanin coloration | absent (Lamuyo) | absent |
| beginning of flowering (1st flower on 2nd flowering node) | late (Daniel, Piquant d'Algérie, Zingaro) | |
| time of maturity | medium (Lamuyo, Latino, Sonar) | |

D. Breeding Sweet Pepper Hybrid 9942595

One aspect of the current invention concerns methods for crossing the sweet pepper hybrid 9942595 and/or pepper lines SBR 99-1260 and SBY 99-1201 with itself or a second plant and the seeds and plants produced by such methods. These methods can be used for propagation of pepper hybrid 9942595 and/or pepper lines SBR 99-1260 and SBY 99-1201, or can be used to produce hybrid pepper seeds and the plants grown therefrom. Hybrid seeds are produced by crossing pepper hybrid 9942595 and/or pepper lines SBR 99-1260 and SBY 99-1201 with a plant of a different genotype as well as by selfing a hybrid.

The development of new varieties using one or more starting varieties is well known in the art. In accordance with the invention, novel varieties may be created by crossing pepper hybrid 9942595 and/or pepper lines SBR 99-1260 and SBY 99-1201, followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are involved.

Uniform lines of new varieties may also be developed by way of double-haploids. This technique allows the creation of true breeding lines without the need for multiple generations of selfing and selection. In this manner true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with pepper hybrid 9942595 and/or pepper lines SBR 99-1260 and SBY 99-1201 and progeny thereof to achieve a homozygous line.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny have the characteristic being transferred, but are like the superior parent for most or almost all other loci. The last backcross generation would be selfed to give pure breeding progeny for the trait being transferred.

The plants of the present invention are particularly well suited for the development of new lines based on the elite nature of the genetic background of these plants. In selecting a second plant to cross with pepper hybrid 9942595 and/or pepper lines SBR 99-1260 and SBY 99-1201 for the purpose of developing novel pepper lines, it will typically be preferred to choose those plants which either themselves exhibit one or more selected desirable characteristics or which exhibit the desired characteristic(s) when in hybrid combination. Examples of desirable traits of sweet peppers include: high seed yield, high seed germination, seedling vigor, early fruit maturity, high fruit yield, ease of fruit setting, disease tolerance or resistance, and adaptability for soil and climate conditions. Consumer-driven traits, such as a preference for a given fruit size, shape, color, texture, and taste, especially non-pungency (low capsaicinoid content), are other traits that may be incorporated into new lines of sweet pepper plants developed by this invention.

Particularly desirable traits that may be incorporated by this invention are improved resistance to different viral, fungal, and bacterial pathogens. Anthracnose and Phytophthora blight are fungal diseases affecting various species of pepper. Fruit lesions and fruit rot are the commercially important aspects of these diseases. Bacterial leaf spot and bacterial wilt are other diseases affecting pepper plants, especially during the wet season. Viral pathogens affecting pepper plants include the Pepper mosaic virus and the Tobacco mosaic virus.

Various genes conferring insect resistance are also known in the art and could be introduced into a pepper plant in accordance with the invention. Insect pests affecting the various species of pepper include the European corn borer, corn earworm, aphids, flea beetles, whiteflies, and mites (Midwest Vegetable Production Guide for Commercial Growers, 2003).

E. Performance Characteristics

As described above, hybrid 9942595 exhibits desirable agronomic traits, including anthocyaninless, a fruit size at maturity from about 200 g to about 300 g and resistance to Races 1 to 3 Bacterial leaf spot (BLS), *Xanthomonas campestris* pv. *vesicatorial*, and Tobacco etch virus (TEV) There are multiple commercial hybrids available with resistance to some, but not all, of these diseases. Resistance as well as other performance characteristics of the line were the subject of an objective analysis of the performance traits of the line relative to other lines. The results of the analysis are presented below.

crossed again to the recurrent parent and the process is repeated until a pepper plant is obtained wherein essentially all of the desired morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol

TABLE 3

Performance Characteristics For Hybrid 9942595

| Line | Source | Race 1-3 BLS resistance | Severe TEV resistance | PeMV resistance | Moderate *Phytophthora capsici* resistance | Antho-cyaninless | Fruit color at green harvest | Fruit size (W × L) in cm | Fruit weight (g.) |
|---|---|---|---|---|---|---|---|---|---|
| 9942595 | Seminis | yes | yes | yes | yes | yes | dark | 10 × 10 | 300 |
| Crusader | Syngenta | yes | no | yes | no | no | dark | 10 × 10 | 300 |
| Revelation | Seminis | yes | yes | yes | yes | no | dark | 11 × 11 | 300 |
| Polaris | Western Seeds | yes | no | no | no | no | dark | 10 × 10 | 300 |

As shown above, hybrid 9942595 exhibits superior resistance to Race 1,2,3 Bacterial Leaf Spot when compared to competing varieties. One important aspect of the invention thus provides seed of the hybrid for commercial use.

F. Further Embodiments of the Invention

In one embodiment of the invention, plants are provided of pepper hybrid 9942595 and/or pepper lines SBR 99-1260 and SBY 99-1201 modified to include at least a first desired heritable trait. Such plants may, in particular embodiments, be developed by a plant breeding technique called backcrossing, wherein essentially all of the desired morphological and physiological characteristics of a variety are recovered in addition to a genetic locus transferred into the plant via the backcrossing technique. The term single locus converted plant as used herein refers to those pepper plants which are developed by a plant breeding technique called backcrossing, wherein essentially all of the desired morphological and physiological characteristics of a variety are recovered in addition to the single locus transferred into the variety via the backcrossing technique.

Backcrossing methods can be used with the present invention to improve or introduce a characteristic into the present variety. The parental pepper plant which contributes the locus for the desired characteristic is termed the nonrecurrent or donor parent. This terminology refers to the fact that the nonrecurrent parent is used one time in the backcross protocol and therefore does not recur. The parental pepper plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (non-recurrent parent) that carries the single locus of interest to be transferred. The resulting progeny from this cross are then will depend on the characteristic or trait being altered and the genetic distance between the recurrent and nonrecurrent parents. Although backcrossing methods are simplified when the characteristic being transferred is a dominant allele, a recessive allele, or an additive allele (between recessive and dominant), may also be transferred. In this instance it may be necessary to introduce a test of the progeny to determine if the desired characteristic has been successfully transferred.

In one embodiment, progeny pepper plants of a backcross in which 9942595 is the recurrent parent comprise (i) the desired trait from the non-recurrent parent and (ii) all of the physiological and morphological characteristics of pepper hybrid 9942595 as determined at the 5% significance level when grown in the same environmental conditions.

Pepper varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

Many single locus traits have been identified that are not regularly selected for in the development of a new inbred but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, modified fatty acid or carbohydrate metabolism, and enhanced nutritional quality. These comprise genes generally inherited through the nucleus.

Direct selection may be applied where the single locus acts as a dominant trait. An example of a dominant trait is the downy mildew resistance trait. For this selection process, the progeny of the initial cross are sprayed with downy mildew spores prior to the backcrossing. The spraying eliminates any plants which do not have the desired downy mildew resistance characteristic, and only those plants which have the downy mildew resistance gene are used in the subsequent backcross. This process is then repeated for all additional backcross generations.

Selection of pepper plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection applicable to the breeding of pepper are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

G. Plants Derived From Sweet Pepper Hybrid 9942595 and Parent Lines Thereof by Genetic Engineering Many useful traits that can be introduced by backcrossing, as well as directly into a plant, are those which are introduced by genetic transformation techniques. Genetic transformation may therefore be used to insert a selected transgene into the pepper line of the invention or may, alternatively, be used for the preparation of transgenes which can be introduced by backcrossing. Methods for the transformation of plants, including pepper plants, are well known to those of skill in the art (see, e.g., Schroeder et al., 1993). Techniques which may be employed for the genetic transformation of pepper plants include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

*Agrobacterium*-mediated transformation of pepper explant material and regeneration of whole transformed pepper plants (including tetraploids) from the transformed shoots has been shown to be an efficient transformation method (U.S. Pat. No. 5,262,316).

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target pepper cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). Transformation of plants and expression of foreign genetic elements is exemplified in Choi et al. (1994), and Ellul et al. (2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for pepper plant gene expression include, but are not limited to, the cauliflower mosaic virus (CaMV) P-35S promoter, which confers constitutive, high-level expression in most plant tissues (see, e.g., Odel et al., 1985), including monocots (see, e.g., Dekeyser et al., 1990; Terada and Shimamoto, 1990); a tandemly duplicated version of the CaMV 35S promoter, the enhanced 35S promoter (P-e35S) the nopaline synthase promoter (An et al., 1988), the octopine synthase promoter (Fromm et al., 1989); and the figwort mosaic virus (P-FMV) promoter as described in U.S. Pat. No.

5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wun1, Siebertz et al., 1989); or (5) chemicals such as methyl jasmonate, salicylic acid, or Safener. It may also be advantageous to employ organ-specific promoters (e.g., Roshal et al., 1987; Schernthaner et al., 1988; Bustos et al., 1989).

Exemplary nucleic acids which may be introduced to the pepper plants of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a pepper plant according to the invention. Non-limiting examples of particular genes and corresponding phenotypes one may choose to introduce into a pepper plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference it their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., 1991). The RNA could also be a catalytic RNA molecule (i.e., a ribozyme) engineered to cleave a desired endogenous mRNA product (see for example, Gibson and Shillito, 1997). Thus, any gene which produces a protein or mRNA which expresses a phenotype or morphology change of interest is useful for the practice of the present invention.

H. Definitions

In the description and tables herein, a number of terms are used. In order to provide a clear and consistent understanding of the specification and claims, the following definitions are provided:

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor or a chemical agent conferring male sterility.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

Resistance: As used herein, the terms "resistance" and "tolerance" are used interchangeably to describe plants that show no symptoms to a specified biotic pest, pathogen, abiotic influence or environmental condition. These terms are also used to describe plants showing some symptoms but that are still able to produce marketable product with an acceptable yield. Some plants that are referred to as resistant or tolerant are only so in the sense that they may still produce a crop, even though the plants are stunted and the yield is reduced.

Regeneration: The development of a plant from tissue culture.

Self-pollination: The transfer of pollen from the anther to the stigma of the same plant.

Single Locus Converted (Conversion) Plant: Plants which are developed by a plant breeding technique called backcrossing, wherein essentially all of the desired morphological and physiological characteristics of a pepper variety are recovered in addition to the characteristics of the single locus transferred in via the backcrossing technique and/or by genetic transformation.

Substantially Equivalent: A characteristic that, when compared, does not show a statistically significant difference (e.g., p=0.05) from the mean.

Tissue Culture: A composition comprising isolated cells of the same or a different type or a collection of such cells organized into parts of a plant.

Transgene: A genetic locus comprising a sequence which has been introduced into the genome of a pepper plant by transformation.

I. Deposit Information

A deposit of pepper hybrid 9942595, disclosed above and recited in the claims, has been made with the American Type Culture Collection (ATCC), 10801 University Blvd., Manassas, Va. 20110-2209. The date of deposit was Oct. 16, 2007. The accession number for those deposited seeds of sweet pepper hybrid 9942595 is ATCC Accession No. PTA-8692. A deposit of pepper line SBR 99-1260, also disclosed herein, has been made with the American Type Culture Collection (ATCC), 10801 University Blvd., Manassas, Va. 20110-2209. The date of deposit was Oct. 16, 2007. The accession number for those deposited seeds of pepper SBR 99-1260 is ATCC Accession No. PTA-8693. A deposit of pepper line SBY 99-1201, also disclosed herein, has been made with the American Type Culture Collection (ATCC), 10801 University Blvd., Manassas, Va. 20110-2209. The date of deposit is May 30, 2008. The accession number for those deposited seeds of pepper line SBY 99-1201, is ATCC Accession No. PTA-9222.

Upon issuance of a patent, all restrictions upon the foregoing deposits will be removed. The deposits are intended to meet all of the requirements of 37 C.F.R. §1.801-1.809. The deposits will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

REFERENCES

The following references, to the extent that they provide exemplary procedural or other details supplementary to those set forth herein, are specifically incorporated herein by reference:

U.S. Pat. No. 5,262,316
U.S. Pat. No. 5,378,619
U.S. Pat. No. 5,463,175
U.S. Pat. No. 5,500,365
U.S. Pat. No. 5,563,055
U.S. Pat. No. 5,633,435
U.S. Pat. No. 5,689,052
U.S. Pat. No. 5,880,275
U.S. Pat. No. 7,087,819
An et al., *Plant Physiol.*, 88:547, 1988.
Berke, *J. New Seeds*, 1:3-4, 1999.
Bird et al., *Biotech. Gen. Engin. Rev.*, 9:207, 1991.
Bustos et al., *Plant Cell*, 1:839, 1989.
Callis et al., *Plant Physiol.*, 88:965, 1988.
Chae et al., *Capsicum Eggplant Newsltr.*, 22:121-124, 2003.
Choi et al, *Plant Cell Rep.*, 13: 344-348, 1994.
Dekeyser et al., *Plant Cell*, 2:591, 1990.
Ellul et al., *Theor. Appl. Genet.*, 107:462-469, 2003.
EP 534 858
Fraley et al., *Bio/Technology*, 3:629-635, 1985.
Fromm et al., *Nature*, 312:791-793, 1986.
Fromm et al., *Plant Cell*, 1:977, 1989.
Gibson and Shillito, *Mol. Biotech.*, 7:125, 1997
Jones and Minisavage, *Phytopathology*, 92(3):273-277, 2002.
Klee et al., *Bio-Technology*, 3(7):637-642, 1985.
Kuhlemeier et al., *Plant Cell*, 1:471, 1989.
Lane et al., *Hortscience*, 32:333-334, 1997.
Marcotte et al., *Nature*, 335:454, 1988.
Marcotte et al., *Plant Cell*, 1:969, 1989.
Midwest Veg. Prod. Guide for Commercial Growers (ID:56), 2003
Odel et al., *Nature*, 313:810, 1985.
Omirulleh et al., *Plant Mol. Biol.*, 21(3):415-428, 1993.
PCT Appln. WO 99/31248
Pandal et al., *Theor. Appl. Gene.*, 68(6):567-577, 1984.
Pickersgill and Barbara, *Euphytica*, 96(1):129-133, 1997
Potrykus et al., *Mol. Gen. Genet.*, 199:183-188, 1985.
Roshal et al., *EMBO J.*, 6:1155, 1987.
Schaffner and Sheen, *Plant Cell*, 3:997, 1991.
Schernthaner et al., *EMBO J.*, 7:1249, 1988.
Siebertz et al., *Plant Cell*, 1:961, 1989.
Simpson et al., *EMBO J.*, 4:2723, 1985.
Terada and Shimamoto, *Mol. Gen. Genet.*, 220:389, 1990.
Uchimiya et al., *Mol. Gen. Genet.*, 204:204, 1986.
Wang et al., *Science*, 280:1077-1082, 1998.
Williams et al., *Nucleic Acids Res.*, 18:6531-6535, 1990.

What is claimed is:

1. A pepper plant comprising at least a first set of the chromosomes of pepper line SBR 99-1260 or pepper line SBY 99-1201, a sample of seed of said lines having been deposited under ATCC Accession Number PTA-8693, and ATCC Accession Number PTA-9222, respectively.

2. A seed comprising at least a first set of the chromosomes of pepper line SBR 99-1260 or pepper line SBY 99-1201, a sample of seed of said lines having been deposited under ATCC Accession Number PTA-8693, and ATCC Accession Number PTA-9222, respectively.

3. The plant of claim 1, which is inbred.

4. The plant of claim 1, which is hybrid.

5. The plant of claim 4, wherein the hybrid plant is pepper hybrid 9942595, a sample of seed of said hybrid 9942595 having been deposited under ATCC Accession Number PTA-8692.

6. The plant of claim 3, wherein the inbred plant is line SBR 99-1260 or line SBY 99-1201.

7. A plant part of the plant of claim 1.

8. The plant part of claim 7, further defined as a leaf, a ovule, pollen, a fruit, or a cell.

9. A pepper plant, or a part thereof, having all the physiological and morphological characteristics of the pepper plant of claim 5.

10. A pepper plant, or a part thereof, having all the physiological and morphological characteristics of the pepper plant of claim 6.

11. A tissue culture of regenerable cells of the plant of claim 1.

12. The tissue culture according to claim 11, comprising cells or protoplasts from a plant part selected from the group consisting of embryos, meristems, cotyledons, pollen, leaves, anthers, roots, root tips, pistil, flower, seed and stalks.

13. A pepper plant regenerated from the tissue culture of claim 12, wherein the plant has all the physiological and morphological characteristics of a pepper plant comprising at least a first set of the chromosomes of pepper line SBR 99-1260 or pepper line SBY 99-1201, a sample of seed of said lines having been deposited under ATCC Accession Number PTA-8693, and ATCC Accession Number PTA-9222, respectively.

14. A method of vegetatively propagating the plant of claim 1 comprising the steps of:
    (a) collecting tissue capable of being propagated from a plant according to claim 1;
    (b) cultivating said tissue to obtain proliferated shoots; and
    (c) rooting said proliferated shoots to obtain rooted plantlets.

15. The method of claim 14, further comprising growing at least a first plant from said rooted plantlets.

16. A method of introducing a desired trait into a pepper line comprising:
    (a) utilizing as a recurrent parent a plant of either pepper line SBR 99-1260 or pepper line SBY 99-1201, by crossing a plant of line SBR 99-1260 or line SBY 99-1201, a sample of seed of said lines having been deposited under ATCC Accession Number PTA-8693, and ATCC Accession Number PTA-9222, respectively, with a second donor pepper plant that comprises a desired trait, to produce $F_1$ progeny;
    (b) selecting an $F_1$ progeny that comprises the desired trait;
    (c) crossing the selected $F_1$ progeny with a plant of the same pepper line used as the recurrent parent in step (a) to produce backcross progeny;
    (d) selecting backcross progeny comprising the desired trait and the physiological and morphological characteristics of the recurrent parent pepper line used in step (a); and
    (e) repeating steps (c) and (d) three or more times to produce selected fourth or higher backcross progeny that comprise the desired trait, and otherwise comprise essentially all of the physiological and morphological characteristics of the recurrent parent pepper line used in step (a).

17. A pepper plant produced by the method of claim 16.

18. A method of producing a plant comprising an added trait, the method comprising introducing a transgene conferring the trait into a plant of hybrid 9942595, line SBR 99-1260 or line SBY 99-1201, a sample of seed of said hybrid and lines having been deposited under ATCC Accession Number PTA-8692, ATCC Accession Number PTA-8693, and ATCC Accession Number PTA-9222, respectively.

19. A plant produced by the method of claim 18.

20. A method of determining the genotype of the plant of claim 1 comprising obtaining a sample of nucleic acids from said plant and detecting in said nucleic acids a plurality of polymorphisms.

21. The method of claim 20, further comprising the step of storing the results of detecting the plurality of polymorphisms on a computer readable medium.

22. A method for producing a seed of a plant derived from at least one of hybrid 9942595, line SBR 99-1260 or line SBY 99-1201 comprising the steps of:
    (a) crossing a pepper plant of hybrid 9942595, line SBR 99-1260 or line SBY 99-1201 with itself or a second pepper plant; a sample of seed of said hybrid and lines having been deposited under ATCC Accession Number PTA-8692, ATCC Accession Number PTA-8693, and ATCC Accession Number PTA-9222, respectively; and
    (b) allowing seed of a hybrid 9942595, line SBR 99-1260 or line SBY 99-1201-derived pepper plant to form.

23. The method of claim 22, further comprising the steps of:
    (c) selfing a plant grown from said hybrid 9942595, line SBR 99-1260 or line SBY 99-1201-derived pepper seed to yield additional hybrid 9942595, line SBR 99-1260 or line SBY 99-1201-derived pepper seed;
    (d) growing said additional hybrid 9942595, line SBR 99-1260 or line SBY 99-1201-derived pepper seed of step (c) to yield additional hybrid 9942595, line SBR 99-1260 or line SBY 99-1201-derived pepper plants; and
    (e) repeating the crossing and growing steps of (c) and (d) to generate at least a first further hybrid 9942595, line SBR 99-1260 or line SBY 99-1201-derived pepper plant.

24. The method of claim 22, wherein the second pepper plant is of an inbred pepper line.

25. The method of claim 22, comprising crossing line SBR 99-1260 with line SBY 99-1201, a sample of seed of said lines having been deposited under ATCC Accession Number PTA-8693, and ATCC Accession Number PTA-9222, respectively.

26. The method of claim 23, further comprising:
    (f) crossing the further hybrid 9942595, line SBR 99-1260 or line SBY 99-1201-derived pepper plant with a second pepper plant to produce seed of a hybrid progeny plant.

27. A hybrid seed produced by the method of claim 25.

28. A plant produced by growing the seed of claim 27.

29. A plant part of the plant of claim 28.

30. The plant part of claim 29, further defined as a leaf, a flower, a fruit, an ovule, pollen, or a cell.

31. The seed of claim 27, wherein one or both of the plant of line SBR 99-1260 or line SBY 99-1201 and the second plant comprises a transgene.

32. The seed of claim 27, wherein one or both of the plant of line SBR 99-1260 or line SBY 99-1201 and the second plant comprises a single locus conversion.

33. A method of producing a pepper seed comprising crossing the plant of claim 1 with itself or a second pepper plant and allowing seed to form.

34. A method of producing a pepper fruit comprising:
    (a) obtaining a plant according to claim 1, wherein the plant has been cultivated to maturity; and
    (b) collecting a pepper from the plant.

35. The method of claim 34, wherein the plant according to claim 1 is a plant of pepper hybrid 9942595, a sample of seed of said hybrid 9942595 having been deposited under ATCC Accession Number PTA-8692.

* * * * *